United States Patent
Klee et al.

(10) Patent No.: US 7,287,441 B2
(45) Date of Patent: Oct. 30, 2007

(54) FOCUSING DEVICE BASED ON BONDED PLATE STRUCTURES

(75) Inventors: Matthew S. Klee, Wilmington, DE (US); Wesley Norman, Landenberg, PA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 11/268,520

(22) Filed: Nov. 8, 2005

(65) Prior Publication Data

US 2006/0053905 A1 Mar. 16, 2006

Related U.S. Application Data

(62) Division of application No. 10/820,014, filed on Apr. 8, 2004, now Pat. No. 6,966,212.

(51) Int. Cl.
*G01N 29/02* (2006.01)
*G01N 1/22* (2006.01)

(52) U.S. Cl. .................... 73/863.11; 73/23.41

(58) Field of Classification Search .... 73/23.39–23.41, 73/23.22, 23.25, 863.11, 31.05, 31.07, 863.12; 422/101; 65/165; 137/334, 338, 339, 341
See application file for complete search history.

(56) References Cited

U.S. PATENT DOCUMENTS 4,916,941 A * 4/1990 Briggs ...................... 73/118.1

| | | | |
|---|---|---|---|
| 4,935,040 A | 6/1990 | Goedert | |
| 5,997,708 A | 12/1999 | Craig | |
| 6,494,078 B1 | 12/2002 | Klee | |
| 6,759,013 B2 | 7/2004 | Kaltenbach et al. | |
| 2001/0008613 A1 | 7/2001 | Kaltenbach et al. | |
| 2002/0187557 A1 | 12/2002 | Hobbs et al. | |

OTHER PUBLICATIONS

Anonymous, "Chemical Analysis Group, 4890 Gas Chromatograph," Agilent Technologies 4890 Specifications Guide, Document A15289, Hewlett-Packard Company, Jun. 1997.
Anonymous, "What Is Gas Chromatography?" Life Sciences/Chemical Analysis Online Store, Agilent Technologies, preprint Oct. 23, 2003 <http://www.chem.Agilent.com/cag/cabu/whatisgc.htm>.
Anonymous, "Chromatography Introductory theory", Sheffield Hallam University School of Science and Mathematics, Division of Chemistry Homepage, preprint Oct. 23, 2003 <http://www.shu.ac.uk/schools/sci/chem /tutorials/chrom/chroml htm>.
Anonymous, "Gas Chromatography", Sheffield Hallam University School of Science and Mathematics, Division of Chemistry Homepage, preprint Oct. 23, 2003 <http://www.shu.ac.uk/schools/sci/chem/tutorials/chrom/gaschrm.htm>.

(Continued)

*Primary Examiner*—Hezron Williams
*Assistant Examiner*—Tamiko Bellamy (57) ABSTRACT

The invention provides a low mass and size thermal focusing device for a gas phase analytical device. The device has two or more plates bonded together. The device also has at least one channel with an entrance and exit is formed within allowing ingress and egress of a gas stream. The device also has a temperature reduction module in thermal contact with at least one plate of the device. Thermal focusing devices with additional plates and/or channels are also disclosed.

5 Claims, 7 Drawing Sheets

OTHER PUBLICATIONS

Maehr, C., "Agilent Technologies announces fastest chromatographic technique available for analyzing purity of fuel-grade ethanol," Agilent Technologies Press Release, May 27, 2003 <http://Agilent.com/about/newsroom/presrel/2003/27may2003b.html>.

Toyoda, S. et al., "Cryogen-Free Automated Gas Chromatograph System for Monitoring of Halocarbons in the Atmosphere at Background Concentration Levels," Analytical Sciences, vol. 14, pp. 917-923, Oct. 1998.

Venter, A., "Chapter 7, The Modulator: Background and literature survey," unpublished Master's Dissertation: Comprehensive Two-Dimensional Supercritical Fluid and Gas Chromatography (SFCxGC), University of Pretoria etd., pp. 110-118, Feb. 15, 2003 <http://upetd.up.ac.za/thesis/available/edt-03132003-161136>.

* cited by examiner

FOCUSING DEVICE BASED ON BONDED PLATE STRUCTURES

This application is a divisional of U.S. patent application Ser. No. 10/820,014, filed Apr. 8, 2004 now U.S. Pat. No. 6,966,212.

BACKGROUND OF THE INVENTION

1. Field of the Invention

The technical field is gas phase analytical instrumentation, and in particular, a focusing device for gas chromatography.

2. Description of Related Art

Gas chromatography is an analytical technique that separates compounds via gas-phase physicochemical processes. Samples comprised of mixtures of compounds are introduced into chromatographic system (sample introduction), vaporized (various means) if not gaseous already, moved by an inert gas stream (carrier gas) into and through a separation column or columns. Sample components separate from each other when they travel through the column at different speeds due to selective interaction with the column and its coating or packing (the stationary phase). Components eluting from the column are then detected by an appropriate detector.

Performance in gas chromatography is often reduced due to spreading of solute bands wider than their theoretically optimal widths. The optimal widths are defined by well understood relationships of column (or column packing) dimensions, carrier gas type (e.g., He, H2, N2) and flow rate, stationary phase type and thickness, and temperature program rates. Sample introduction devices (inlets) that transfer sample into the analytical column dictate the initial bandwidth of the sample. If sample introduction is slow, such as with splitless injection modes, headspace analysis, thermal desorption, etc., then some sort of focusing technique is required to narrow the input bandwidth sufficiently to be appropriate for the given analytical system being used for separation. As solute bands move through the column, they naturally spread further. The degree of spreading in the column is well modeled by known relationships. In some applications, it is advantageous to narrow the width of solute bands eluting from one column as it passes to another column, a detector, or other zone. Having a narrow initial bandwidth in the subsequent zone will often enhance chromatographic performance.

Various means for correcting for band spreading, that has occurred in one section, prior to release into another section have been developed. Methods for correcting band spreading or narrowing the bands are often referred to as focusing. Current focusing methods, however, all have disadvantages and limitations.

Focusing is typically accomplished through some combination of thermal focusing and solvent focusing. The migration of solutes slows approximately 2-fold for every 25° C. decrease in temperature. So, in simple terms, thermal focusing works based on the principle that solutes tend to "stick" to the stationary phase if temperatures are significantly lower than their elution temperatures. Temperatures at least 50° C. less than the elution temperatures is typically recommended, however, the lower the temperature, the less mobile the solute and the more effective the focusing.

Solvent focusing relies on re-condensation of evaporated solvent in the head of the column. This requires that the condensation zone be below the boiling point of the solvent. The lower the temperature below the boiling point of the solvent, the faster the condensation process and more confined the solvent (and therefore solute) zone. The condensed solvent acts to re-dissolve solutes that were evaporated in the chromatographic inlet. Evaporation expands the volume of a liquid several hundred times as it goes into the gaseous state. Re-condensation and re-dissolution reverse that effect, thereby reducing the volume several hundred times as the vapors enter the cooled zone.

Thermal focusing or "cold trapping" in GC is known. However there are limitations to the currently practiced trapping techniques. In one common implementation, the entire oven area of the instrument is cooled. This effectively turns the entire contents of the oven into a trap. This is useful for focusing broad bands that are caused by slow sample introduction (sample introduction device being outside the oven). However this implementation can not be easily be applied to focusing separated bands eluting from one column prior to passing them to another (multidimensional chromatography) and require large amounts of cooling and heating because the whole oven area and contents are temperature cycled.

Another common implementation is to direct cryogen (or another cooling gas) on a small section or column in the oven using a jet. The oven stays at whatever higher temperature it is set at, while the small section of column experiences a lower local temperature. Although more applicable to multidimensional chromatography, this approach usually consumes a large amount of coolant and at the same time requires more power from the oven heater to compensate for the cooling of the cryogen being added to the oven.

Another approach is to use electro-thermal devices in contact with a short section of column in the oven. This suffers from high failures and such devices have limited temperature cycling range (especially when in a heated oven environment).

SUMMARY OF THE INVENTION

The invention provides a low mass and size thermal focusing device for a gas phase analytical device. The device has two or more plates bonded together. The device also has at least one channel with an entrance and exit is formed within allowing ingress and egress of a gas stream. The device also has a temperature reduction module in thermal contact with at least one plate of the device.

BRIEF DESCRIPTION OF DRAWINGS

The invention will be described in detail in the following description of preferred embodiments with reference to the following figures.

DETAILED DESCRIPTION OF PREFERRED EMBODIMENTS

Figure 1:
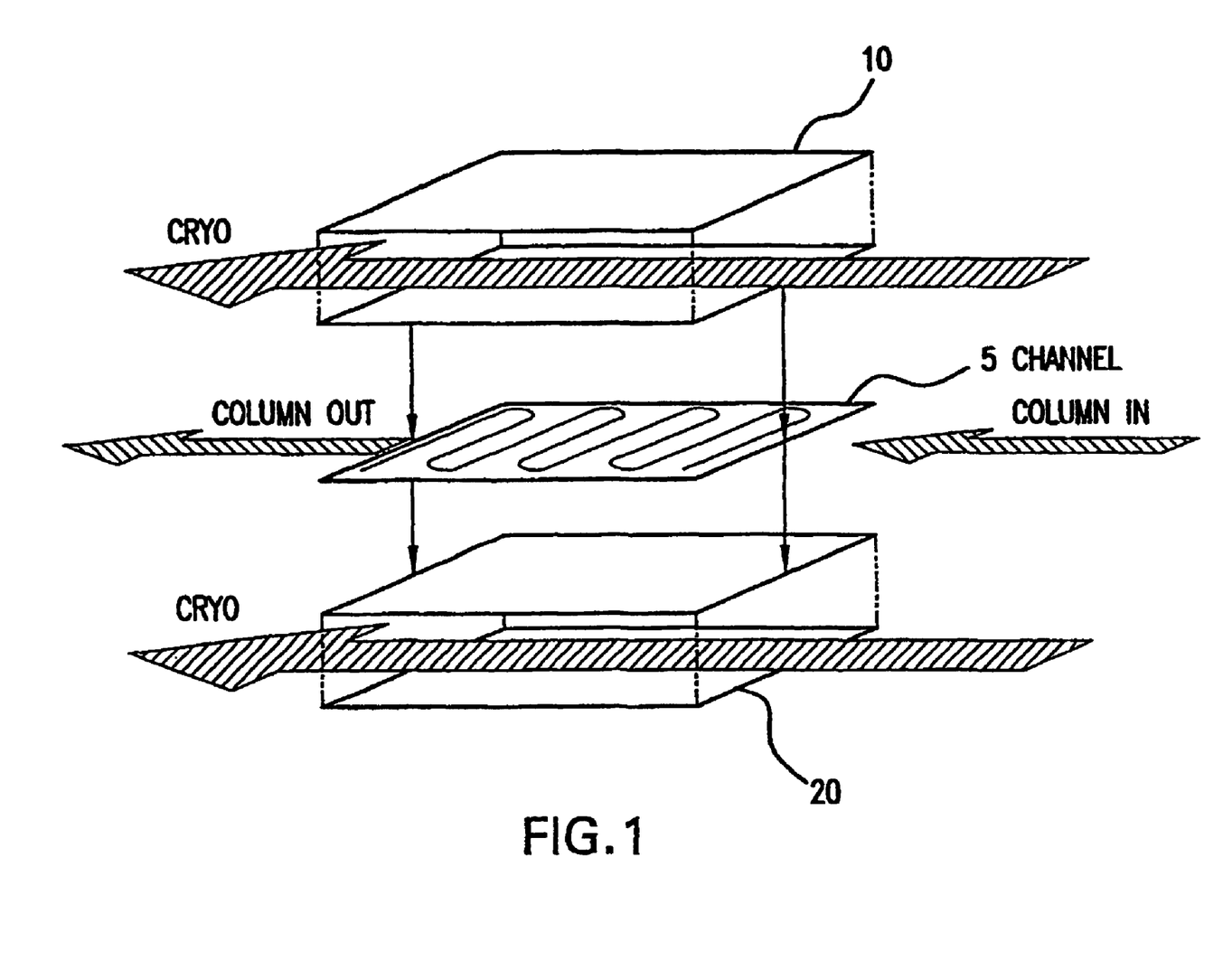
FIG. 1 is a diagram of the features of the present invention.

A focusing device for a gas phase analytical device is disclosed. The basic design of the diffusion bonded plate cryogenic device is illustrated in FIG. 1. FIG. 1 show an isolated inert sample path 5 embedded between two diffusion bonded plates 10 and 20 with cryogenic zones above and/or below. Within the basic design there is great flexibility of the physical configuration of the plates, sample path(s) dimensions (length and width of channel), and cryogen expansion zone(s). Specific embodiments illustrating the flexibility of the present invention are disclosed below. These embodiments are only examples and do not limit the scope of the invention.

Figure 2:
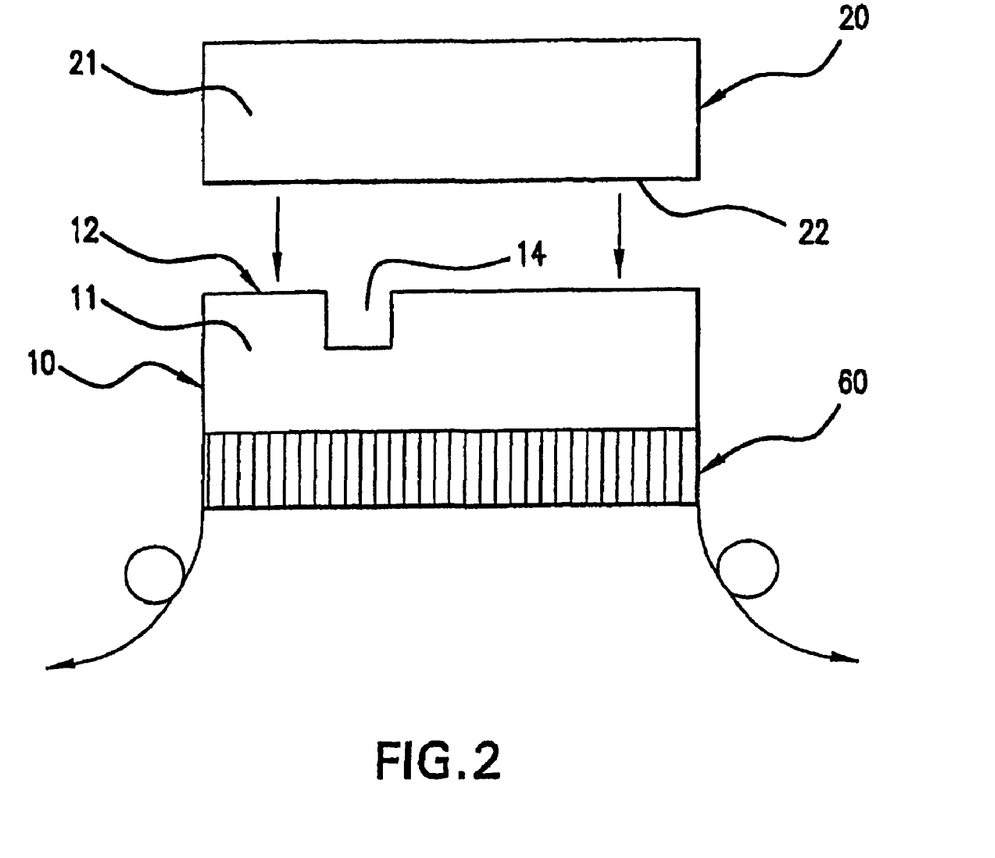
FIG. 2 is a side view of one embodiment of the present invention utilizing two plates.

In one embodiment, sample paths 5 are created by etched depressions on plates 10 that are then sandwiched and sealed with other plates 20 in which channels have been etched, or alternatively to flat plates 20. FIG. 2 shows an exploded side view of two plates 10 and 20 of a focusing device of the present invention. As shown, the plates 10 and 20 are not yet sealed. The first plate 10 has a first surface 12. A channel 14 is etched into the first surface 12. The channel 14 begins at one end and extends in a continuous path to an exit, preferably on the opposite end (not shown) of the plate 10. The channels and features are added to a face of a stainless steel plate or variety of substrates typically using a variant of the photolithography methods used in the chem-milling of printed circuit boards or printing plates used in offset press technology. Use of a substrate such as stainless steel has inherent advantages relating to ruggedness, flexibility in integrating several different functions within one device, ease of manufacturing, inertness, compatibility with several common and proprietary forms of deactivation, and lifetime.

The second plate 20 has a second surface 22 that is flat and has substantially the same dimensions as the first surface 12. The first plate 10 is fixed to the second plate 20 by sealing the first surface 12 to the second surface 22. Bonding is accomplished by various welding techniques, for example, diffusion bonding, in the case of stainless steel substrates. Other materials, e.g. Ceramics, silicon, polymers, etc, can be bonded by various welding techniques. Once sealed, a sample path is created with an inlet and outlet to the sample path that permits ingress and egress of a gas stream into the device. In one embodiment, chromatographic columns are connected to the inlet and the outlet. The depth and/or width of the channel 14 can be varied to create a larger bored sample pathway. Additionally, the length of the channel can increased by etching, for example, a serpentine or zigzag pattern, as opposed to a straighter channel, to create a longer sample path.

Preferably, the sample flow path is inert for highest impact on the desired application space. Inertness of the sample flow path can be achieved through various deactivation means. One way, for example, is to use plates made out of inert material. Another possible method for achieving inertness is to apply a thin coating of an inert substance on surfaces in contact with sample. Preferred thin coating substances include silica (e.g., SilicoSteel®), Sulfinert™, titanium nitride, and gold plating, although many other suitable materials could be used. Alternatively, or in combination with other techniques, coatings of inert substance can be applied to improve focusing and increase inertness. Preferred coating substances include common stationary phases and common GC packing materials (e.g., porous polymers, coated packings, etc.). Any one of these methods for achieving inertness can be used alone or in combination for greater effectiveness. In yet another embodiment, a pathway of the device serves as a housing for a length of chromatographic column that can be inserted and then later removed and replaced with a substitute length of column. Larger bore channels and even larger channel free enclosures within bonded plates can be formed to serve as housing for a trapping column.

Key to effective focusing is lowering of the temperature of the device. The device in FIG. 2. has in thermal contact with the first plate 10 an electro-thermal device 60, for example a Peltier, for cooling the sample path for focusing and optionally heating it for desorption. Other methods and means for both heating and cooling are discussed in more detail below. This can be accomplished in a number of ways with the present invention. The nature of the design concept generally describe described in FIG. 1 accommodates optimization of the design for many different coolant approaches. Plate dimensions, the number of layers of plates, the pathway(s) for coolant and restrictions necessary for efficient expansion of cryogens, etc. can all be accommodated within the design concepts.

Figure 3:
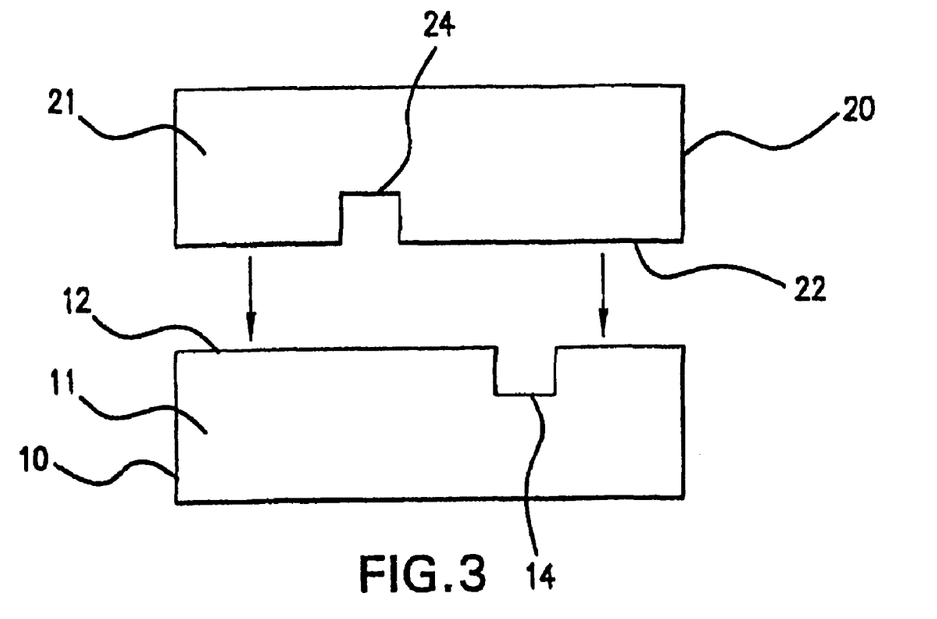
FIG. 3 is a side view of an additional two plate embodiment of the present invention.
Figure 4:
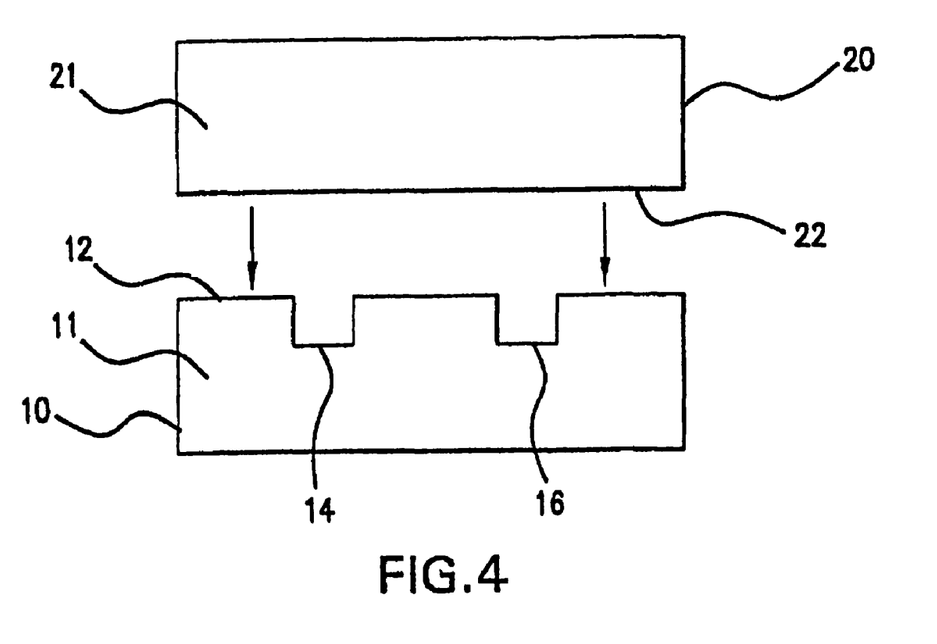
FIG. 4 is a side view of an additional two plate embodiment of the present invention.
Figure 5:
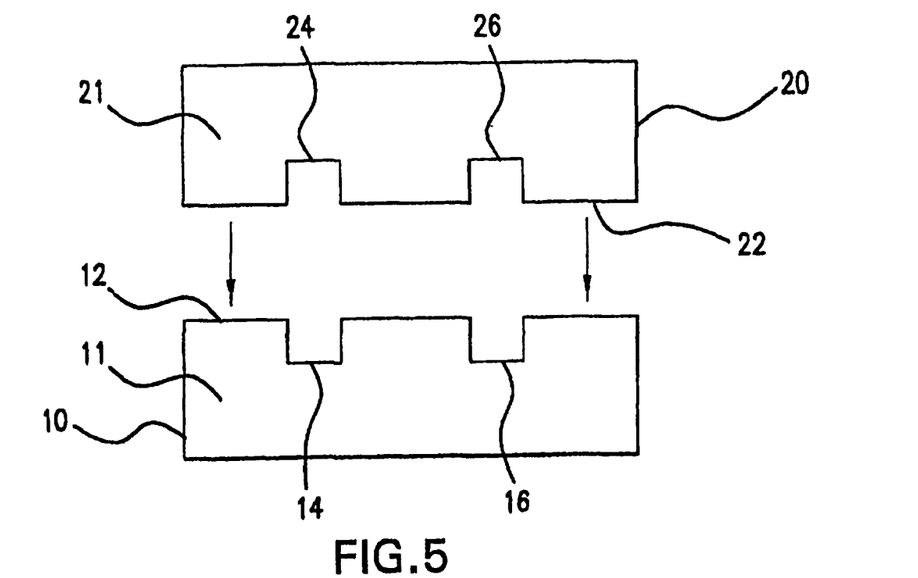
FIG. 5 is a side view of an additional two plate embodiment of the present invention.

FIGS. 3–5 illustrate additional embodiments utilizing two plates bonded together, similar to FIG. 2. In each embodiment two paths are created when the plates are bonded, one pathway for sample and a second for coolant. The difference between the embodiments disclosed in FIG. 3–5 and FIG. 2 is the location of the etching to create the channels that will form the sample and/or coolant paths. FIG. 3 shows the side view of two plates 10 and 20. A first channel 14 is etched into the first surface 12 of the first plate 10. The channel begins (or ends) at the side 11 of the first plate 10. And, and as shown in FIG. 2, extends in a continuous path to an exit in a different side, preferably at the opposite end. The exit and entrance of the channel can be in any side, and even on the same side in some embodiments. In FIG. 3 a second channel 24 is etched into the second surface 22 of the second plate 20. The channel begins (or ends) at the side 21 of the second plate 20. Like the first channel 14, the second channel extends in a continuous path to an exit. When the first plate 10 is bonded and sealed to the second plate 20 in the direction indicated by the arrows, two paths are created. The channels 14 and 24 are positioned so that the channels 14 and 24 do not intersect at any point in the device.

FIG. 4 shows another two plate embodiment, that when assembled is also a two pathway device. In this embodiment the first channel 14 is positioned on the first surface 12 of the first plate 10. A second channel 16 that does not intersect with the first channel 14 is also positioned on the first surface 12 of the first plate 10. The second plate 20 is a solid plate of substantially the same length and width of the first plate 10. The second surface 22 of the second plate 20 is bonded to the first surface 12 of the first plate 10 in the direction of the arrows. The resulting device has two paths in the place of the channels.

FIG. 5 shows yet another two plate embodiment, that when assembled is a two pathway device. The first plate 10 and second plate 20 have substantially the same length and width. In this embodiment, like FIG. 4, a first and second channel 14 and 16 are positioned on the first surface 12 of the first plate 10. The second plate 20 has a second surface 22. A third channel 24 and fourth channel 26 are etched in the second surface at locations corresponding to the first channel 14 and second channel 16 respectively. When bonded two paths are formed. In this way paths with larger diameters can be formed from similarly dimensioned plates to the embodiment in FIG. 4.

A two path device, such as those describe in FIGS. 3–5 can accommodate an incorporated cooling means. In a two path device, one path may be used as a sample path, and the second path can be used for the introduction of a coolant to focus the sample. The coolant path preferably runs parallel to the sample path for the most efficient cooling. Many types of coolant gases and sources may be used effectively.

For most effective cooling, cryogens are used as the coolant. Typical cryogens include evaporation of liquid $CO_2$ and liquid $N_2$, and are suitable for use with the devices of the present invention. Different cryogens have different design requirements for most efficient use and are familiar to those skilled in the art. The different restrictions necessary for expansion of the two gases can easily be integrated into the plate design.

An alternative coolant is compressed air blown through coolant channel of the focusing device to lower its temperature. This is a more cost efficient method but has thermal limitations. It is most effective if the temperature of the compressed air is significantly lower than the temperature of the device (e.g., the GC oven temperature is >150° C. hotter than the air), but this is not a requirement.

An alternative approach for cooling the device is vortex cooling. In terms of effectiveness of cooling, vortex cooling is somewhere between the use of cryogens and the use of compressed air. In vortex cooling, a vortex tube creates a vortex from compressed air and then separates it into hot and cold airstreams. On entering a vortex tube, the compressed air flow passes through a vortex generation chamber, which starts the air stream rotating. The air stream exiting the chamber rotates at very high speeds (e.g., speeds up to 1,000,000 rpm) as it is forced along the inner walls of the tube towards a control valve. At the control valve, a small portion of the air exits through a needle valve as hot exhaust. The remaining air is forced back through the center of the incoming air stream at a slower speed, where the slower moving return air gives up heat energy to the faster moving incoming air. The cooled return air then flows through the center of the vortex generation chamber and exits through the cold air exhaust port. The cold air can then be flowed through the path in the device. Vortex cooling typically reduces incoming temperatures 35–45° C., making it quite suitable for use with the invention in certain applications.

The present invention lends itself to a number of cooling options in addition to those described above, such as, for example, Peltier cooling described in FIG. 1, the use of refrigerants and others.

Once focused, solutes must be desorbed effectively from the device. This is accomplished through heating. The present invention accommodates several approaches to heating. The simplest is to merely stop the flow of coolant and let the device equilibrate with its ambient (e.g., GC oven) temperature. The invention works well with this approach due to its low thermal mass and uniform heat conduction but may not be ideal for every application.

Faster and higher temperature heating of the device can be accomplished by direct heating. When the device is designed with electrically conductive materials, an electrical current can be driven across the device, which operates to heat up the device. Appropriate control and temperature sensing circuits are typically used when controlled heating is desired.

In another embodiment indirect heating can be used. This is especially appropriate when non-conductive materials or unsuitable materials are used to construct the device. For example heat traces can be integrated into the device, or heating cartridges can be attached, as well as other indirect heating methods. Typically, appropriate temperature feedback and control devices would be used with indirect heating as well.

Other heating approaches are also possible, and suitable, with the disclosed device. For one example, if cold effluent from a vortex generator is used to cool the device, the hot effluent flow could also be used to heat the device. In an analogous manner, a Peltier could be reversed to supply heat for desorption. In another embodiment, if refrigerant is used to cool the device, the process could be reversed to supply heat in a manner similar to heat pumps, with the condensing coils either attached to or designed within the device.

Just as the invention can accommodate many types of cooling and heating methods, the present invention has great flexibility with the construction of the device. For example, two plate embodiments have been described. The present invention can be configured using more than two plates. For example, FIG. 6 illustrates one three plate embodiment.

Figure 6:
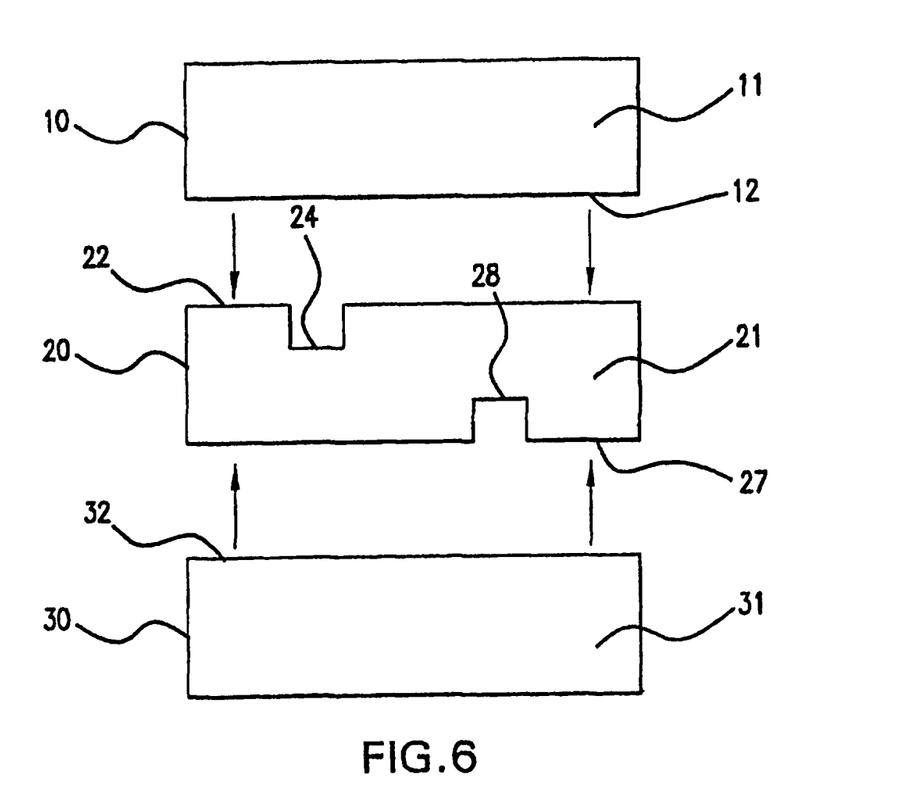
FIG. 6 is a side view of a three plate embodiment of the present invention.

In FIG. 6, a first plate 10, a second plate 20, and a third plate 30 are bonded together to form the device. The first plate 10 has a first surface 12. The second plate 20 has two surfaces 22 and 27. A first channel 24 is etched into the first surface 22 and a second channel 28 is etched in the second surface 27. The third plate 30 has a first surface 32 and side 31. The first plate 10 and the third plate 30 are bonded to the second plate in the direction of the arrows forming two pathways on either surface of the second plate 20.

FIG. 6 is only one illustration of a three plate embodiment; other embodiments utilizing three or more plates is contemplated by the present invention. Many different configurations of plates and channel placements are possible to achieve the desired combination of channel length and diameter necessary for effective focusing. For example, a three plate embodiment can have more than one path between each plate. Longer paths can be formed in a such a three plate device by providing the appropriate feed through holes from one pathway and connections to a separate pathway in the same device.

Figure 7:
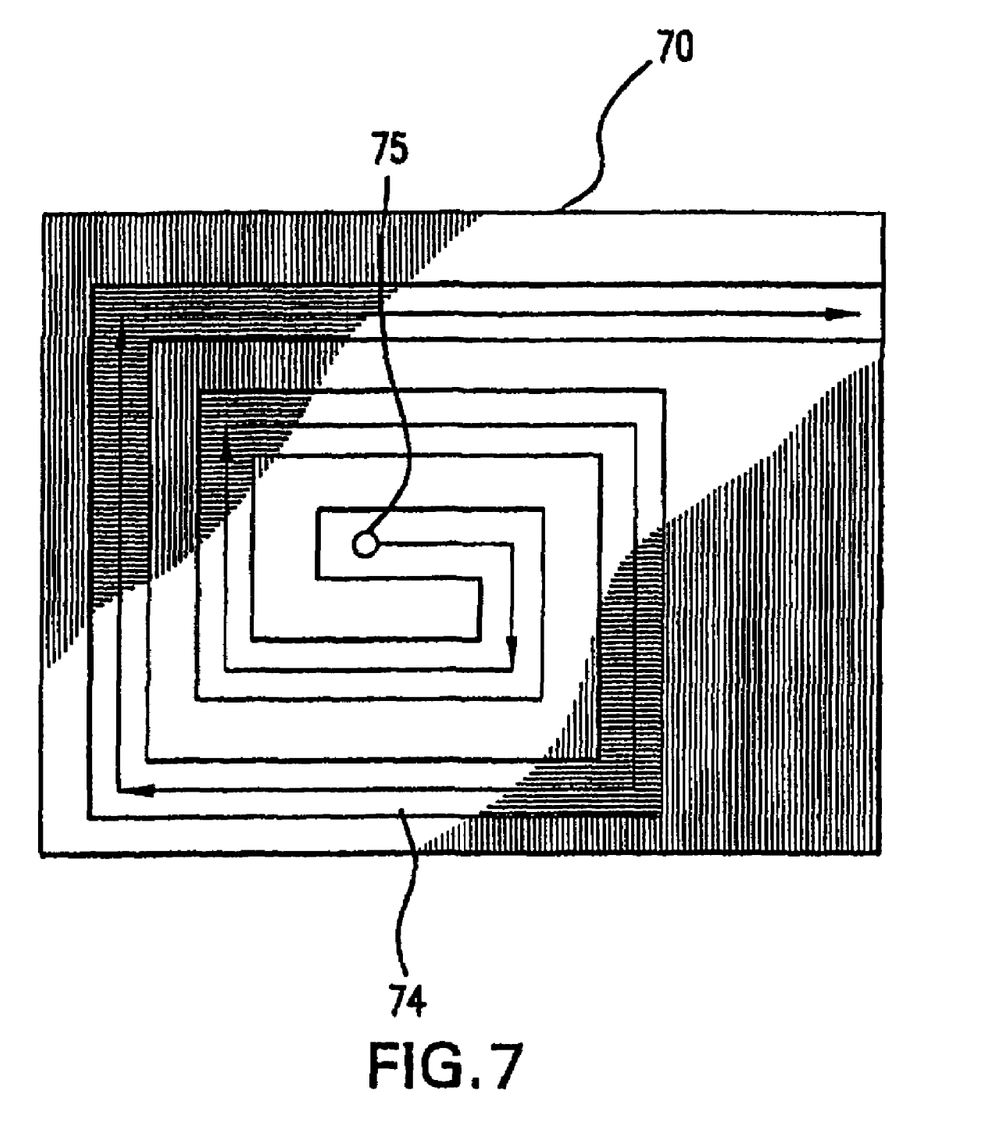
FIG. 7 is a top view of a plate with material removed to form a slot.

In yet another embodiment sample paths can be achieved by completely removing material (creating slots) on the plate, and then sandwiching the plate between two other solid plates to create a pathway in the device. In this approach, alternating slotted plates with solid plates can yield larger paths. FIG. 7 illustrates a plate 70 with a slot 74 created by the removal of material from the plate 70. A center point 75 is positioned to receive a feed through hole.

Figure 8:
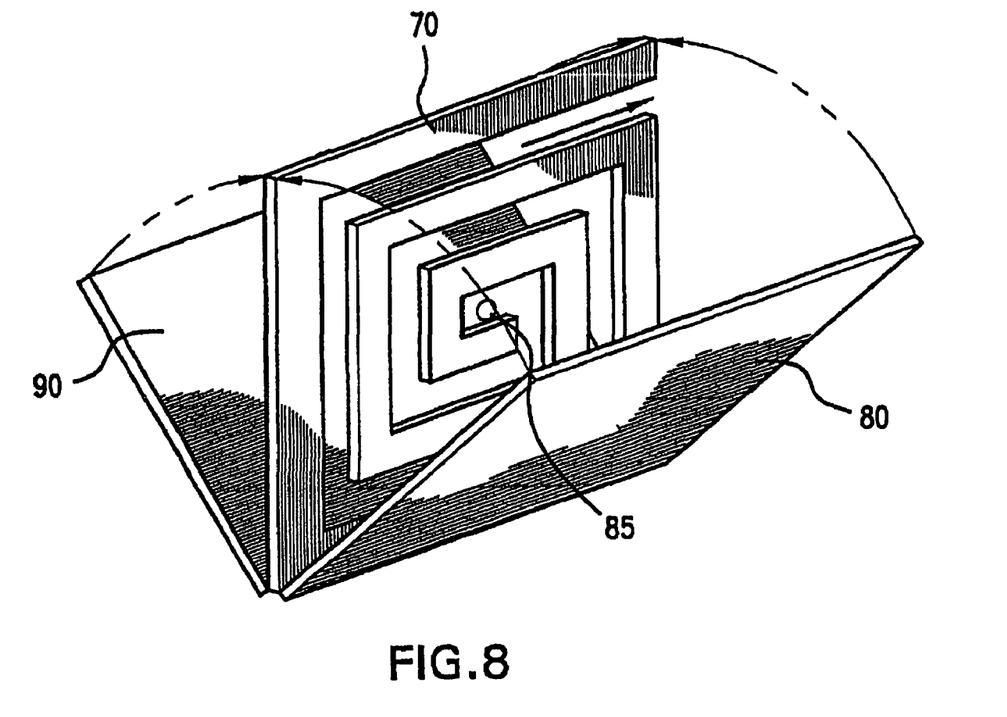
FIG. 8 is a perspective view of a three plate embodiment of the present invention.
Figure 9:
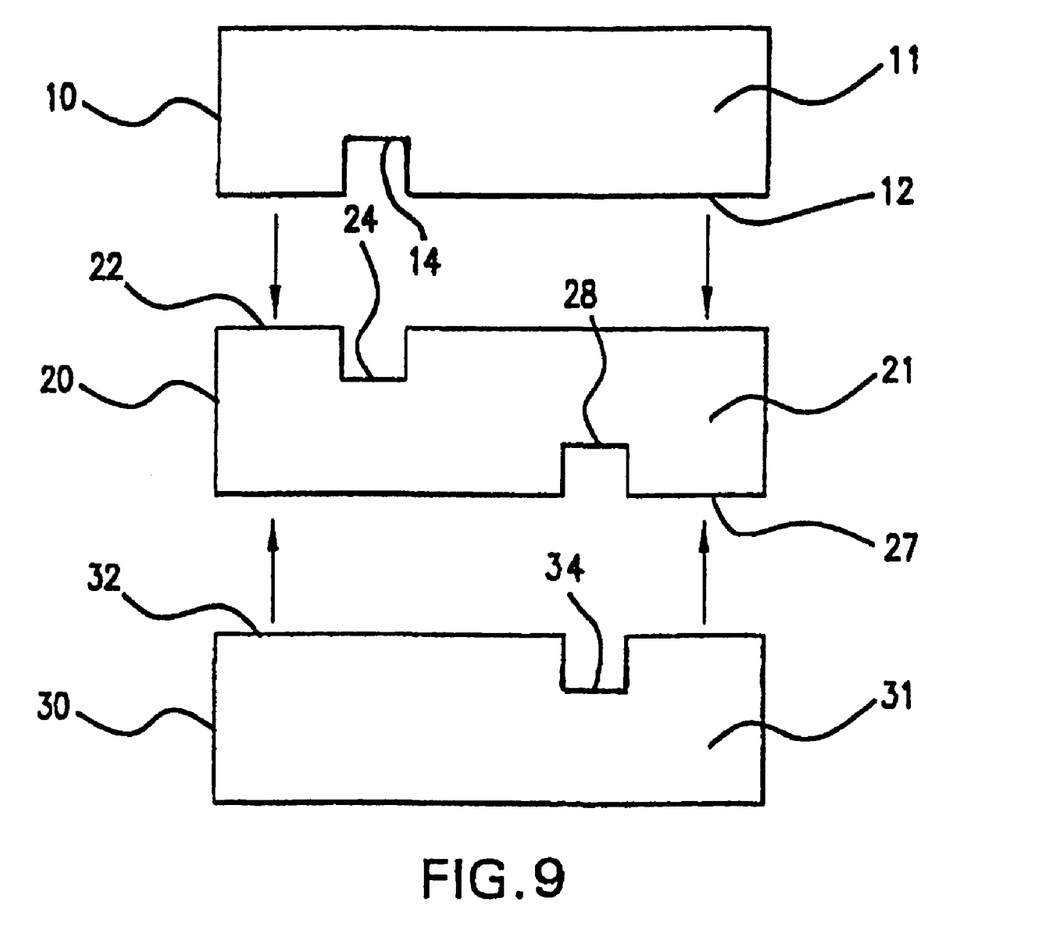
FIG. 9 is a perspective view of another three plate embodiment of the present invention.

FIG. 8 illustrates the plate 70 and the two outside plates 80 and 90. Plates 80 and 90 are bonded in the direction of the arrows and create a sample path. A feed through hole at 85 is lined up with the center 75 of the plate 70. Plate 90 is solid with no breaks or holes. Additional plates (not shown) can be added as desired to create additional pathways if desired.

The disclosed invention can be integrated with other fluidic devices. For example, a natural combination is to couple a Deans switch for multidimensional GC with the cryofocusing device of the present invention. Additional combinations are possible including effluent splitters, combiner of multiple flows (focusing effluent from several streams into a single place).

Having described preferred embodiments of a novel focusing device for gas chromatography (which are intended to be illustrative and not limiting), it is noted that modifications and variations can be made in light of the above teachings. It is therefore to be understood that changes may be made in the particular embodiments of the invention disclosed which are within the scope of the invention as defined by the appended claims.

Having thus described the invention with the details and particularity required by the patent laws, what is claimed and desired protected by Letters Patent is set forth in the appended claims.

What is claimed is:

1. A method comprising:
    passing a first fluid through a first channel in a device, the first fluid being one of a cryogen and a coolant; and
    trapping a gas sample within a second channel in the device,
    wherein the passing of the first fluid through the first channel includes expanding the cryogen within the first channel.

2. A method according to claim 1, further comprising desorbing the gas sample from the second channel.

3. A method according to claim 2, wherein the desorbing of the gas sample includes heating the device.

4. A method according to claim 3, wherein the heating of the device includes passing an electric current through the device.

5. A method according to claim 3, wherein:
    the heating of the device includes passing a second fluid through a third channel in the device;
    the second fluid is hotter than the first fluid;
    the passing of the first fluid ceases at or before the passing of the second fluid begins.

* * * * *